United States Patent
Sharma et al.

(10) Patent No.: US 12,042,166 B2
(45) Date of Patent: Jul. 23, 2024

(54) MEDICAL ARTICULATION DEVICES AND METHODS OF USING THE SAME

(71) Applicant: Boston Scientific Medical Device Limited, Galway (IE)

(72) Inventors: Deepak Kumar Sharma, Muzaffarnagar (IN); James J. Scutti, Norwell, MA (US); Sharath Kumar G, Kanakapura (IN)

(73) Assignee: BOSTON SCIENTIFIC MEDICAL DEVICE LIMITED, Galway (IE)

( * ) Notice: Subject to any disclaimer, the term of this patent is extended or adjusted under 35 U.S.C. 154(b) by 4 days.

(21) Appl. No.: 17/480,276

(22) Filed: Sep. 21, 2021

(65) Prior Publication Data

US 2022/0087703 A1 Mar. 24, 2022

Related U.S. Application Data

(60) Provisional application No. 63/081,807, filed on Sep. 22, 2020.

(51) Int. Cl.
*A61B 17/29* (2006.01)
*A61B 17/00* (2006.01)

(52) U.S. Cl.
CPC .... *A61B 17/2909* (2013.01); *A61B 2017/003* (2013.01); *A61B 2017/2902* (2013.01);
(Continued)

(58) Field of Classification Search
CPC ........ A61B 17/2909; A61B 2017/2902; A61B 2017/2911; A61B 2017/2924;
(Continued)

(56) References Cited

U.S. PATENT DOCUMENTS 6,569,105 B1 5/2003 Kortenbach et al.
8,333,780 B1 12/2012 Pedros et al.
(Continued)

FOREIGN PATENT DOCUMENTS

EP 2147638 A1 1/2010
EP 3636163 A1 4/2020

OTHER PUBLICATIONS

International Search Report and Written Opinion issued on Nov. 25, 2021, in counterpart International Patent Application No. PCT/IB2021/058602 (14 pages, in English).

*Primary Examiner* — Shaun L David
*Assistant Examiner* — Rachael L Geiger
(74) *Attorney, Agent, or Firm* — Bookoff McAndrews, PLLC

(57) ABSTRACT

A medical device that includes a handle, a shaft extending distally from the handle, an end effector extending distally from the shaft, a first actuator movably coupled to the handle, and a second actuator movably coupled to the handle. The first actuator is configured to (1) articulate the shaft in response to translating the first actuator in a first direction relative to the handle and the second actuator, and (2) actuate the end effector in response to translating the first actuator in a second direction relative to the handle and the second actuator. The second actuator is configured to (1) articulate the shaft in response to translating the second actuator in the first direction relative to the handle and the first actuator, and (2) actuate the end effector in response to translating the second actuator in the second direction relative to the handle and the first actuator.

19 Claims, 4 Drawing Sheets

(52) U.S. Cl.
CPC ............... *A61B 2017/2911* (2013.01); *A61B 2017/2924* (2013.01)

(58) Field of Classification Search
CPC .... A61B 2017/003; A61B 2017/00305; A61B 2017/00309; A61B 2017/00318; A61B 2017/00331; A61B 2017/00323; A61B 2017/00327; A61B 2017/00424; A61B 2017/291; A61M 25/015; A61M 25/0147; A61M 25/0102; A61M 25/0136; A61M 25/0132
See application file for complete search history.

(56) References Cited

U.S. PATENT DOCUMENTS

| | | |
|---|---|---|
| 2009/0171161 A1 | 7/2009 | Ewers et al. |
| 2013/0237907 A1* | 9/2013 | Bacher ............... A61B 17/2909 604/95.04 |
| 2014/0094658 A1 | 4/2014 | Nomura |
| 2015/0105809 A1* | 4/2015 | Connolly .......... A61M 25/0147 606/159 |
| 2016/0174970 A1* | 6/2016 | Shelton, IV ..... A61B 17/07207 227/180.1 |
| 2019/0076160 A1* | 3/2019 | Lin .................... A61B 17/2909 |

* cited by examiner

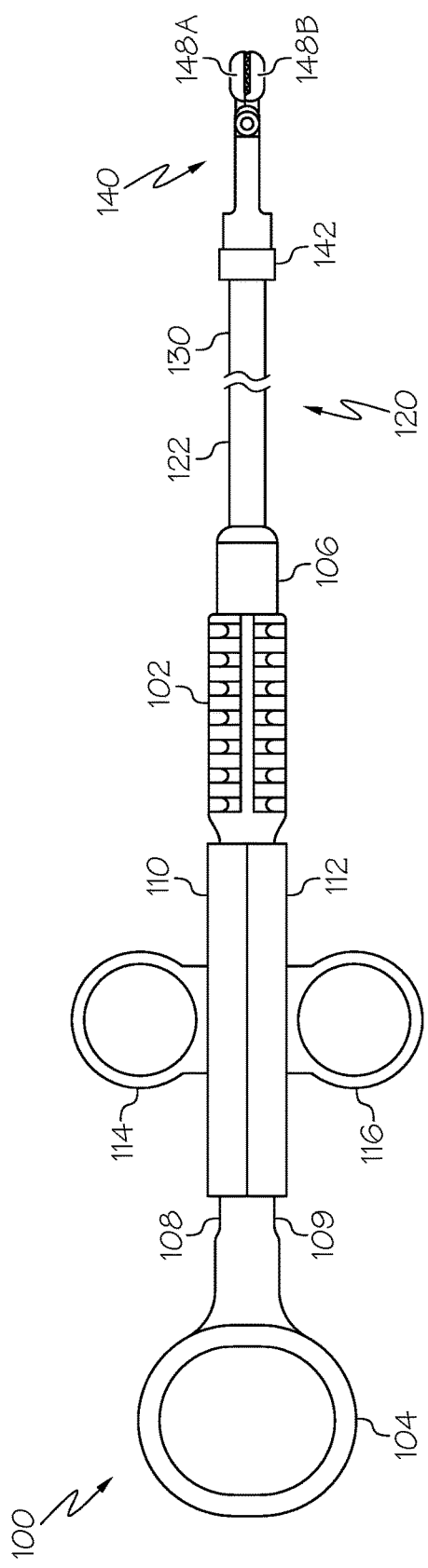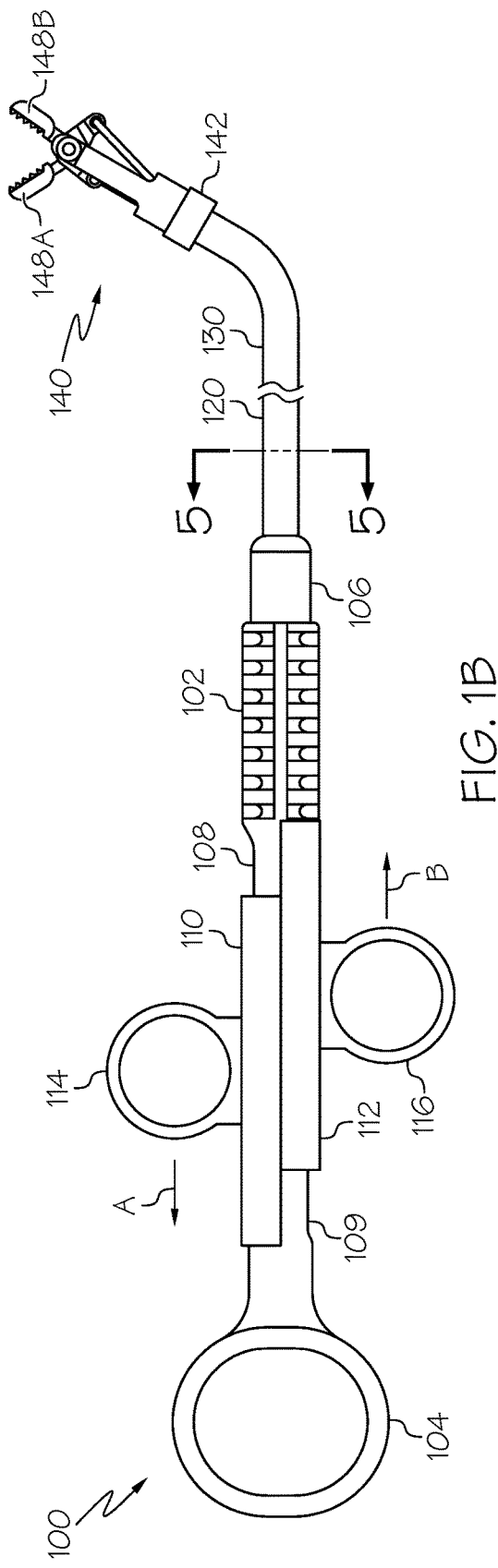
FIG. 1A
FIG. 1B

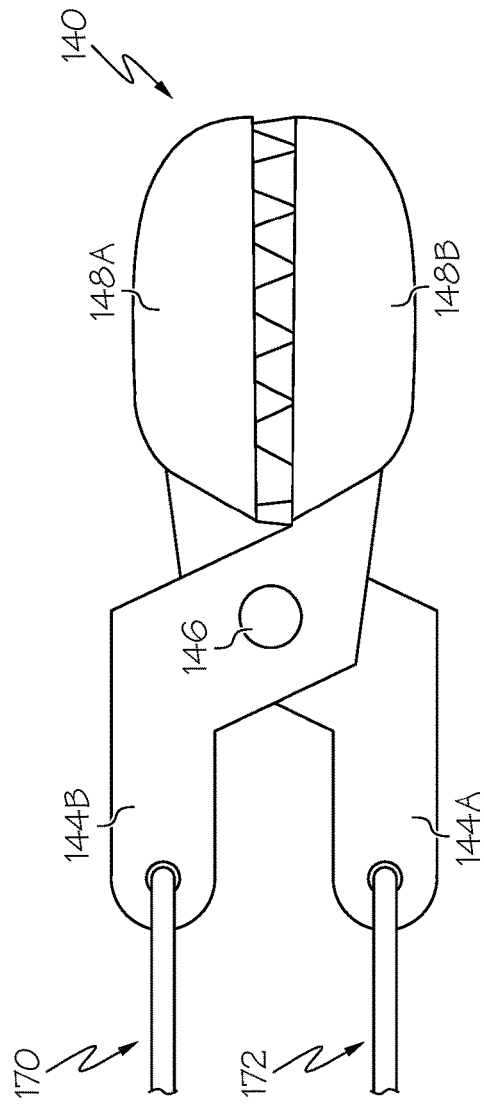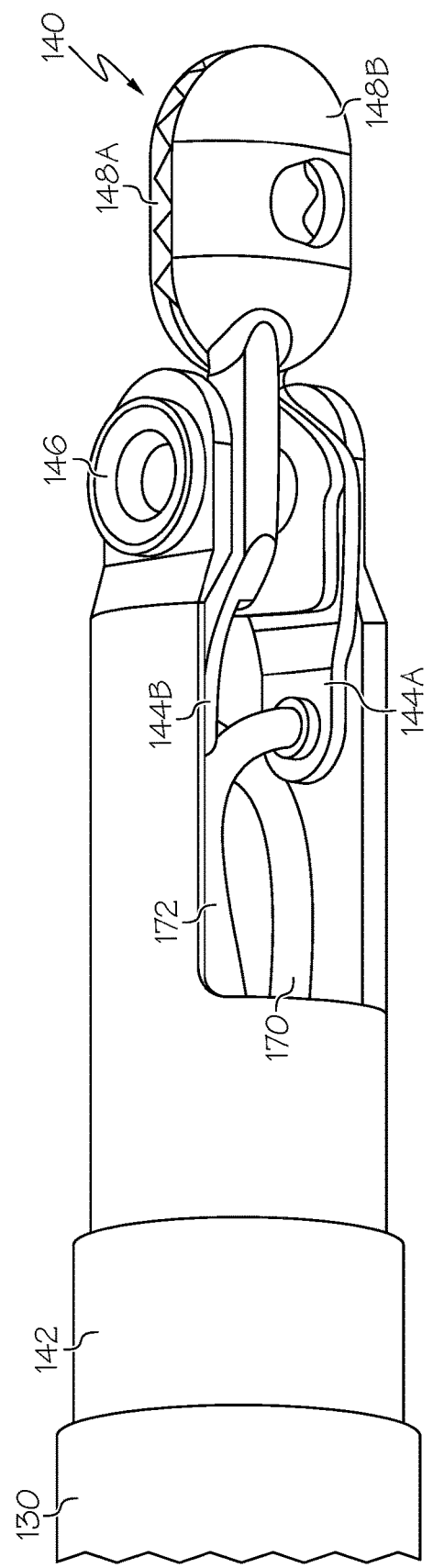

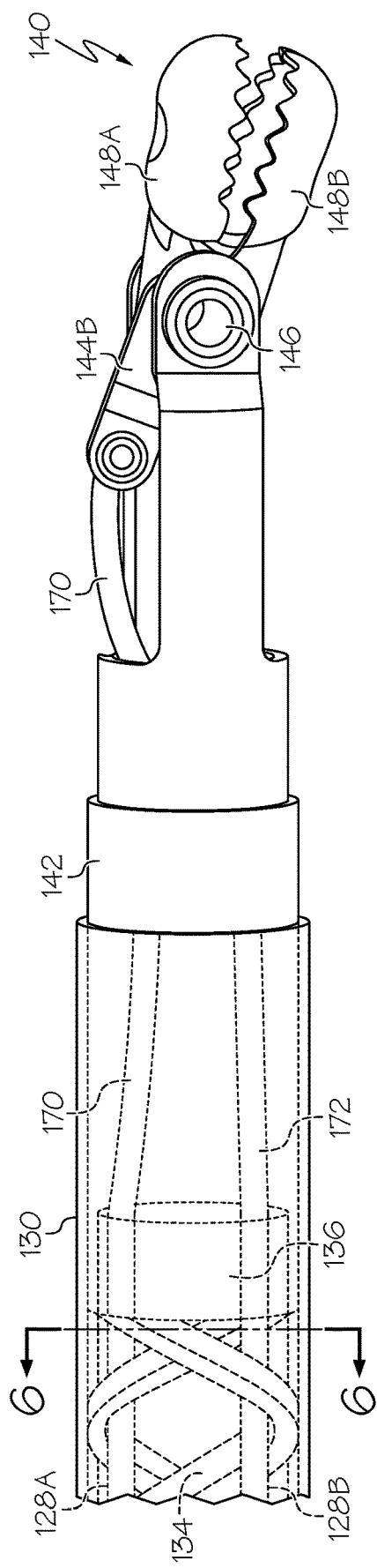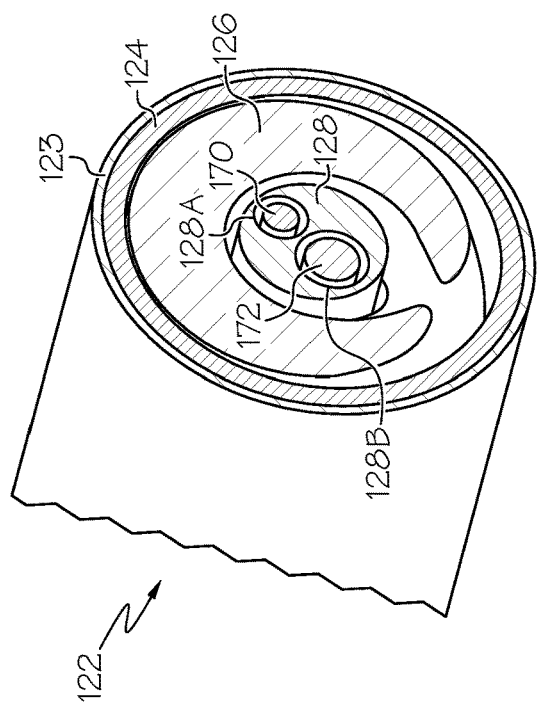

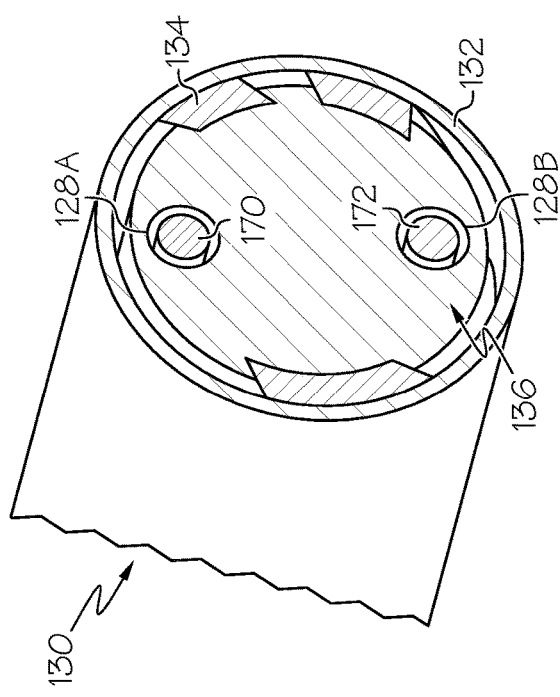
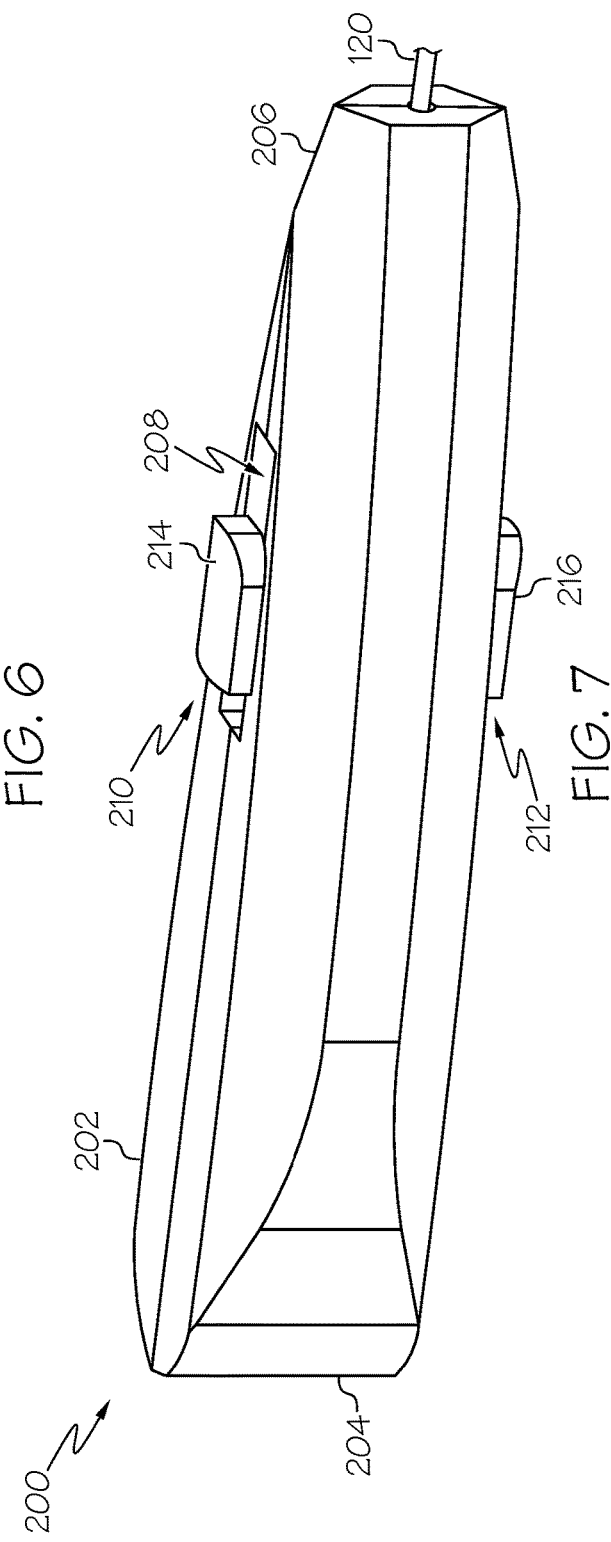

MEDICAL ARTICULATION DEVICES AND METHODS OF USING THE SAME

CROSS-REFERENCE TO RELATED APPLICATIONS

This application claims the benefit of priority of U.S. Provisional Patent Application No. 63/081,807, filed Sep. 22, 2020, the entirety of which is incorporated herein by reference.

TECHNICAL FIELD

Various aspects of the disclosure relate generally to medical articulation systems, devices, and related methods. Examples of the disclosure relate to systems, devices, and related methods for articulating a medical tool relative to a subject, among other aspects.

BACKGROUND

Endoscopic and surgical procedures of the gastrointestinal (GI) tract include, for example, submucosal dissection, colonic resection, bariatric surgery, esophagectomy, gastric bypass, and sleeve gastrectomy, among others. These procedures may involve lifting and/or removing tissue from the body of a patient. Accessory devices for performing such procedures may include complex interfaces for operating said device. Further, the interfaces may provide limited articulating capabilities for maneuvering the device within the patient, thereby requiring use of additional devices or multiple hands to manipulate said device.

SUMMARY

Aspects of the disclosure relate to, among other things, systems, devices, and methods for treating a target treatment site using an articulating device providing enhanced degree of maneuverability, among other aspects. Each of the aspects disclosed herein may include one or more of the features described in connection with any of the other disclosed aspects.

According to an example, a medical device includes a handle, a shaft extending distally from the handle, an end effector extending distally from the shaft, a first actuator movably coupled to the handle, and a second actuator movably coupled to the handle. The first actuator is configured to (1) articulate the shaft in response to translating the first actuator in a first direction relative to the handle and the second actuator, and (2) actuate the end effector in response to translating the first actuator in a second direction relative to the handle and the second actuator. The second actuator is configured to (1) articulate the shaft in response to translating the second actuator in the first direction relative to the handle and the first actuator, and (2) actuate the end effector in response to translating the second actuator in the second direction relative to the handle and the first actuator.

Any of the medical devices described herein may include any of the following features. The handle includes a first track extending along a body of the handle. The first actuator is received within the first track and configured to translate along the first track. The first track has a longitudinal length that corresponds to (1) a first degree of articulation of the shaft; and (2) a first extent of actuation of the end effector. The handle includes a second track extending along the body of the handle. The second actuator is received within the second track and configured to translate along the second track. The second track has a longitudinal length that corresponds to (1) a second degree of articulation of the shaft; and (2) a second extent of actuation of the end effector. Further including a first wire and a second wire disposed within the handle and the shaft. The first wire is coupled to the first actuator and a first part of the end effector. The second wire is coupled the second actuator and a second part of the end effector. The first actuator is configured to move the first wire in the first direction to articulate the shaft and move the first part and the second part in the first direction. The second actuator is configured to move the second wire in the second direction to move the second part relative to the first part. The second actuator is configured to move the second wire in the first direction to articulate the shaft and move the first part and the second part in the first direction. The first actuator is configured to move the first wire in the second direction to move the second part relative to the first part. The first actuator is configured to move the first part relative to the second part, and the second actuator is configured to move the second part relative to the first part. The first actuator is configured to articulate the shaft toward the first actuator and in the first direction in response to translating the first actuator in the first direction relative to the handle and the second actuator. The second actuator is configured to articulate the shaft toward the second actuator and in the first direction in response to translating the second actuator in the first direction relative to the handle and the first actuator. The first actuator and the second actuator are disposed about a circumference of the handle. The first actuator and the second actuator are at least partially disposed within the handle. The first actuator includes a first finger ring, the second actuator includes a second finger ring, and the handle includes a third finger ring. The third finger ring is fixed relative to the first and second finger rings, and the first and second finger rings are move relative to one another and the third finger ring. The first actuator has a proximalmost position corresponding to an articulated position of the shaft, a distalmost position corresponding to an actuated position of the end effector, and a neutral position between the proximalmost position and the distalmost position, and corresponding to an unarticulated position of the shaft and an unactuated position of the end effector.

According to another example, a medical device includes a handle having a first movable actuator and a second movable actuator, a shaft extending distally from the handle and having an end effector at a distal end of the shaft, a first wire disposed within the shaft and coupled to the first movable actuator and the end effector, and a second wire disposed within the shaft and coupled to the second movable actuator and the end effector. The first movable actuator is configured to (1) articulate the shaft in response to translating the first wire proximally relative to the shaft and the second movable actuator, and (2) actuate the end effector in response to translating the first wire distally relative to the shaft and the second movable actuator. The second movable actuator is configured to (1) articulate the shaft in response to translating the second wire proximally relative to the shaft and the first movable actuator, and (2) actuate the end effector in response to translating the second wire distally relative to the shaft and the first movable actuator.

Any of the medical devices described herein may include any of the following features. The handle includes a first track and a second track extending along opposing sides of the handle. The first movable actuator is received within the first track and configured to translate along the first track, and the second movable actuator is received within the second track and configured to translate along the second track. The first track has a first longitudinal length that corresponds to (1) a first degree of articulation of the shaft; and (2) a first extent of actuation of the end effector. The second track has a second longitudinal length that corresponds to (1) a second degree of articulation of the shaft; and (2) a second extent of actuation of the end effector. The first movable actuator is configured to articulate the shaft toward the first movable actuator and in the first direction in response to translating the first actuator in the first direction relative to the handle and the second actuator. The second movable actuator is configured to articulate the shaft toward the second movable actuator and in the first direction in response to translating the second actuator in the first direction relative to the handle and the first actuator.

According to a further example, a medical device includes a handle having a first longitudinal track and a second longitudinal track, a shaft extending distally from the handle, an end effector at a distal end of the shaft, and a first actuator coupled to a first wire disposed within the shaft. The first actuator translates along the first longitudinal track. The medical device includes a second actuator coupled to a second wire disposed within the shaft. The second actuator translates along the second longitudinal track. The first actuator is configured to retract the first wire proximally relative to the shaft to articulate the shaft in a first direction when the first actuator moves proximally in the first longitudinal track and the second actuator is fixed relative to the second longitudinal track. The second actuator is configured to retract the second wire proximally relative to the shaft to articulate the shaft in a second direction when the second actuator moves proximally in the second longitudinal track and the first actuator is fixed relative to the first longitudinal track. The second direction is opposite of the first direction.

It may be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate exemplary aspects of the disclosure and together with the description, serve to explain the principles of the disclosure.

FIG. 1A is a side view of an exemplary medical device including a pair of actuators, a handle, and an effector in an actuated (closed) state and an unarticulated position, according to aspects of this disclosure;

FIG. 1B is a side view of the medical device of FIG. 1A with the end effector in an unactuated (open) state and an articulated position, according to aspects of this disclosure;

FIG. 2 is a side view of the end effector of the medical device of FIG. 1A including a pair of wires, according to aspects of this disclosure;

FIG. 3 is a perspective view of the end effector of the medical device of FIG. 1A in the actuated (closed) state, according to aspects of this disclosure;

FIG. 4 is a perspective view of the end effector of the medical device of FIG. 1A in the unactuated (open) state, with each of the pair of wires disposed within a shaft of the medical device, according to aspects of this disclosure;

FIG. 5 is a cross-sectional perspective view of a proximal shaft of the medical device of FIG. 1A, according to aspects of this disclosure;

FIG. 6 is a cross-sectional perspective view of a distal articulation joint of the medical device of FIG. 1A, according to aspects of this disclosure; and FIG. 7 is a perspective view of a handle of another exemplary medical device in, according to aspects of this disclosure.

DETAILED DESCRIPTION

In ESD, an object in the GI tract is targeted for removal, such as, for example, a tumor. A medical device capable of removing the target object is received in a medical instrument (e.g., an endoscope) that is endoscopically placed through the GI tract and at the target treatment site. An ancillary device may be placed endoscopically at the target treatment site for manipulating tissue surrounding the target object. Ancillary devices and systems suited for ESD are limited, however. The disclosure, however, is not limited to ESD procedures, and instead can be used in any suitable medical procedure.

Examples of the disclosure include systems, devices, and methods for manipulating materials and/or objects (e.g., tissue) at a target treatment site within a subject (e.g., patient) with enhanced degree of maneuverability. In examples, ESD includes endoluminal placement of an end effector, e.g., a jaw assembly or other like tool at the target treatment site. Placement of the end effector may be via a catheter, scope (endoscope, bronchoscope, colonoscope, etc.), tube, or sheath, inserted into the GI tract via a natural orifice. The orifice can be, for example, the nose, mouth, or anus, and the placement can be in any portion of the GI tract, including the esophagus, stomach, duodenum, large intestine, or small intestine. Placement also can be in other organs or other bodily spaces reachable via the GI tract, other body lumens, or openings in the body.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a patient. By contrast, the term "proximal" refers to a portion closest to the user when placing the device into the subject. As used herein, the terms "comprises," "comprising," or any other variation thereof, are intended to cover a non-exclusive inclusion, such that a process, method, article, or apparatus that comprises a list of elements does not necessarily include only those elements, but may include other elements not expressly listed or inherent to such process, method, article, or apparatus. The term "exemplary" is used in the sense of "example," rather than "ideal." As used herein, the terms "about," "substantially," and "approximately," indicate a range of values within +/−10% of a stated value.

Examples of the disclosure may relate to devices and methods for performing various medical procedures and/or treating portions of the large intestine (colon), small intestine, cecum, esophagus, any other portion of the gastrointestinal tract, and/or any other suitable patient anatomy (collectively referred to herein as a "target treatment site"). As mentioned above, this disclosure is not limited to any specific medical device or method, and aspects of the disclosure may be used in connection with any suitable medical tool and/or medical method, at any suitable site within the body. Various examples described herein include single-use or disposable medical devices.

FIGS. 1A-1B show an exemplary medical device 100 in accordance with an example of this disclosure. Medical device 100 may include a handle 102 having a longitudinal length defined by a proximal end 104 and a distal end 106. Proximal end 104 may include a grasping feature that is configured to facilitate manual control of handle 102. For example, the grasping feature may include a ring that is sized and shaped to receive a finger of the user of medical device 100. Handle 102 may further include a pair of tracks 108, 109 positioned along opposing sides of handle 102 and extending between proximal end 104 and distal end 106. As described further herein, tracks 108, 109 may define a travel path of one or more actuators 110, 112, and a longitudinal length of tracks 108, 109 may define an articulation and actuation extent of medical device 100.

Medical device 100 may further include a pair of actuators 110, 112 movably coupled to handle 102 at tracks 108, 109. For example, medical device 100 may include a first actuator 110 slidably coupled to first track 108, and a second actuator 112 slidably coupled to second track 109. First actuator 110 may be configured to translate along first track 108, and second actuator 112 may be configured to translate along second track 109, in one or more directions A, B. That is, each of first actuator 110 and second actuator 112 may move in either a first direction A or a second direction B. First actuator 110 and second actuator 112 may be configured to move independently of, and relative to, one another. Actuators 110, 112 may be actuated in various suitable manners and sequences, such as simultaneously and/or separately from one another. In some embodiments, first actuator 110 and second actuator 112 may be disposed about a circumference of handle 102 and collectively enclose at least a portion of handle 102 therebetween.

Although not shown, it should be understood that first actuator 110 may be coupled to a first wire 170 received within handle 102, and second actuator 112 may be coupled to a second wire 172 received within handle 102 (see FIGS. 2-4). Wires 170, 172 may be coupled to actuators 110, 112 via various suitable mechanism, including, for example, crimping, an adhesive, ultrasonic curing, etc. Accordingly, each actuator 110, 112 may be configured to move the corresponding wire 170, 172 relative to handle 102 in response to translating along the respective track 108, 109.

Still referring to FIGS. 1A-1B, first actuator 110 may include a body with a grasping feature 114 extending laterally outward from the body of first actuator 110. Second actuator 112 may include a body with a grasping feature 116 extending laterally outward from the body of second actuator 112. Each grasping feature 114, 116 may be configured to facilitate movement of the respective actuator 110, 112 relative to the corresponding track 108, 109. In the example, each grasping feature 114, 116 may include a ring that is sized and shaped to receive a corresponding finger of a user of medical device 100. It should be appreciated that grasping features 114, 116 may have various other suitable sizes, shapes, and/or configurations without departing from a scope of this disclosure.

Medical device 100 may include a shaft 120 fixed to and extending distally from handle 102, and particularly from distal end 106. Shaft 120 may include a proximal shaft 122 and a distal articulation joint 130. A proximal end of proximal shaft 122 may extend be coupled to distal end 106, and a proximal end of distal articulation joint 130 may be coupled to a distal end of proximal shaft 122. Medical device 100 may further include an end effector 140 coupled to a distal end of distal articulation joint 130. End effector 140 may include one or more parts, such as a clevis 142, a first jaw 148A, and a second jaw 148B. Clevis 142 may be secured to the distal end of distal articulation joint 130, and jaws 148A, 148B may be pivotably coupled to clevis 142. As described further herein, each jaw 148A, 148B may be movable in response to translation of actuators 110, 112. In the embodiment, end effector 140 may exclude one or more links coupled to the pair of jaws 148A, 148B. As described further herein, medical device 100 may be configured to enhance a grasping force between jaws 148A, 148B from the exclusion of links in end effector 140.

Referring now to FIGS. 2-3, each jaw 148A, 148B may be coupled to at least one of the actuators 110, 112 via the corresponding wire 170, 172. For example, first jaw 148A may be coupled to second actuator 112 via second wire 172, and second jaw 148B may be coupled to first actuator 110 via first wire 170. In the example, first jaw 148A may include a proximal arm 144A that receives second wire 172, and second jaw 148B may include a proximal arm 144B that receives first wire 170. Accordingly, it should be understood that end effector 140 excludes links (or any other structures) between jaws 148A, 148B and wires 170, 172, such that wires 170, 172 are coupled directly to jaws 148A, 148B at the corresponding proximal arm 144A, 144B. Medical device 100 may be operable to minimize a mechanical loss of force transfer between actuators 110, 112 and jaws 148A, 148B from the exclusion of one or more links (or any other structures) between wires 170, 172 and jaws 148A, 148B.

It should be appreciated that end effector 140 is depicted in FIG. 2 with clevis 142 omitted for illustrative purposes only. End effector 140 may include a pin 146 defining a pivot point of jaws 148A, 148B, i.e., jaws 148A, 148B may be movably coupled to one another about pin 146. Further, first jaw 148A and second jaw 1486 may be movably coupled to clevis 142 at pin 146. Each jaw 148A, 148B may include a plurality of teeth along an interior surface for grasping an object disposed between jaws 148A, 148B, such as, for example, tissue. It should be understood that end effector 140 may include various suitable configurations, including, but not limited to, one or more clamps, shears, forceps, scissors, suturing devices, lighting devices, imaging systems, grasper assemblies, and various other suitable tools and/or devices. Accordingly, end effector 140 shown and described herein is merely exemplary such that medical device 100 may include various other end effectors without departing from a scope of this disclosure.

Referring now to FIG. 4, first wire 170 and second wire 172 may be disposed within shaft 120, and extend distally from distal articulation joint 130 to couple with proximal arms 144B, 144A, respectively. In the example, shaft 120 may include a first lumen 128A configured to receive first wire 170, and a second lumen 128B configured to receive second wire 172. It should be understood that movement of first actuator 110 along handle 102 may provide movement of first wire 170 within first lumen 128A and a corresponding movement of second jaw 148B. Further, movement of second actuator 112 along handle 102 may provide movement of second wire 172 within second lumen 128B and a corresponding movement of first jaw 148A. As described in detail herein, each of first actuator 110 and second actuator 112 may be configured to actuate end effector 140 and articulate distal articulation joint 130. Additionally, as described in further detail below, shaft 120 (e.g., proximal shaft 122, distal articulation joint 130) may include one or more inner layers, including a first inner layer 134 that is in a braided configuration and a second inner layer 136 (e.g., multi-lumen shaft) that defines first lumen 128A and second lumen 128B.

Referring now to FIG. 5, proximal shaft 122 is depicted with a plurality of layers. In the example, proximal shaft 122 may include an outer layer 123, a first inner layer 124, a second inner layer 126, and a third inner layer 128. Outer layer 123 may be disposed about first inner layer 124, and may be configured to insulate first inner layer 124, such as, for example, from a tool (e.g., cautery knife) positioned adjacent to medical device 100. In some examples, outer layer 123 may be formed of an insulating material, such as, for example, reflow including Pebax® resin. Outer layer 123 may be further formed of a material having a predefined hardness ranging from about 10 D (durometer) to about 100 D, and more particularly 30 D to 75 D. In other embodiments, outer layer 123 may be omitted entirely.

First inner layer 124 may be disposed about second inner layer 126, and may include a braid formed of a plurality of wires (e.g., flat, round, etc.) braided to one another. In some examples, first inner layer 124 may include a plurality of wires ranging from about 10 wires to about 100 wires, and more particularly 16 to 32 wires. In some embodiments, a braiding of first inner layer 124 may be angled, such as at an angle ranging from about 10 degrees to about 100 degrees, and more particularly 30 to 50 degrees. The braiding of first inner layer 124 may be in various suitable patterns, including, for example, a diamond braid, a Hercules braid, and more. First inner layer 124 may be configured to increase a torque and/or stiffness of proximal shaft 122. In other embodiments, first inner layer 124 may be omitted entirely.

Still referring to FIG. 5, second inner layer 126 may be disposed about third inner layer 128, and may include a coil that is wound (e.g., clockwise, counter clockwise, etc.) about third inner layer 128. In some embodiments, a coil pitch of second inner layer 126 may be substantially similar to a wire diameter of the coil. Second inner layer 126 may be configured to provide a rigidity to proximal shaft 122.

Third inner layer 128 may be formed of polytetrafluoroethylene (PTFE) and include first lumen 128A and second lumen 128B for receiving each of first wire 170 and second wire 172, respectively. In the example, the lumens of third inner layer 128 may have similar and/or different diameters relative to one another. Third inner layer 128 may include a diameter ranging from about 0.5 millimeters to about 1.0 millimeters, and particularly 0.8 millimeters. First lumen 128A may include a diameter ranging from about 0.2 millimeters to about 0.8 millimeters, and particularly 0.4 millimeters, and second lumen 128B may include a diameter ranging from about 0.1 millimeters to about 0.7 millimeters, and particularly 0.3 millimeters. In other embodiments, third inner layer 128 may be omitted entirely or in lieu of a pair of sheaths each defining a lumen for receiving at least one of wires 170, 172.

Still referring to FIG. 5, first wire 170 and second wire 172 may be formed of various materials, including, for example, stainless steel, Nitinol, plastic, aluminum, etc. In some examples, first wire 170 and/or second wire 172 may be coated with PTFE and/or other suitable materials. Additionally, first wire 170 and/or second wire 172 may each include a single wire or may be a multi-strand wire assembly. As described in further detail herein, each of first wire 170 and second wire 172 may be configured to provide articulation of shaft 120 and actuation of end effector 140.

Referring now to FIG. 6, distal articulation joint 130 is depicted with a plurality of layers. In the example, distal articulation joint 130 may include an outer layer 132, a first inner layer 134, and a second inner layer 136. Outer layer 132 may be disposed about first inner layer 134, and may be configured to insulate first inner layer 134. For example, outer layer 132 may be formed of an insulating material, such as, for example, reflow including Pebax® resin. Outer layer 132 may be formed of a material having a predefined hardness that is relatively less than outer layer 122 of proximal shaft 122. For example, outer layer 132 may have a predefined hardness ranging from about 5 D to about 100 D, and more particularly 30 D to about 50 D. As described in detail herein, distal articulation joint 130 may be configured to bend relative to proximal shaft 122 in response to an actuation of at least one of wires 170, 172.

First inner layer 134 may be disposed about second inner layer 136, and may include a braid formed of a plurality of wires (e.g., flat, round, etc.) braided to one another. First inner layer 134 may be substantially similar to first inner layer 124. For example, first inner layer 134 may include a plurality of wires ranging from about 10 wires to about 100 wires, and more particularly 16 to 32 wires. In other examples, first inner layer 134 may include fewer wires than first inner layer 124. First inner layer 134 may be configured to increase a torque and/or stiffness of distal articulation joint 130. In some embodiments, a braiding of first inner layer 134 may be angled, such as at an angle ranging from about 10 degrees to about 100 degrees, and more particularly 30 to 50 degrees. The braiding of first inner layer 134 may be in various suitable patterns, including, for example, a diamond braid, a Hercules braid, and more.

Still referring to FIG. 6, second inner layer 136 may be formed of polytetrafluoroethylene (PTFE), and may include first lumen 128A and second lumen 128B for receiving each of first wire 170 and second wire 172, respectively. In the example, first lumen 128A and second lumen 128B of second inner layer 136 may have similar and/or different diameters relative to one another. In other embodiments, second inner layer 136 may be omitted entirely or in lieu of a pair of sheaths each defining a lumen for receiving at least one of wires 170, 172. Second inner layer 136 may be formed of a material having a predefined hardness ranging from about 15 D to about 95 D, and more particularly 33 D to 50 D. First wire 170 may extend distally from second inner layer 136 and through clevis 162 for engagement with proximal arm 144B (see FIGS. 2-3). First wire 170 may be secured to proximal arm 144B by an adhesive, welding, crimping, ultraviolet (UV) curing, etc. Second wire 172 may extend distally from second inner layer 136 and through clevis 162 for engagement with proximal arm 144A (see FIGS. 2-3). Second wire 172 may be secured to proximal arm 144A by an adhesive, welding, crimping, ultraviolet (UV) curing, etc.

According to an exemplary method of using medical device 100, a medical instrument (e.g., an endoscope) may be initially navigated through the body of a subject to position a distal end of the medical instrument at a target treatment site. Medical device 100 may be received within the medical instrument and end effector 140 may extend outwardly from the distal end of the medical instrument. In this instance, end effector 140 may be positioned within the subject and at the target treatment site while handle 102 is positioned external from the subject at a proximal end of the medical instrument. It should be appreciated that end effector 140 will be maintained in an actuated (closed) state during delivery through the medical instrument.

Referring now to FIG. 1A, first actuator 110 and second actuator 112 may each be positioned in a first position relative to handle 102 such that distal articulation joint 130 is maintained in an unarticulated state (e.g., a longitudinal axis of distal articulation joint 130 is aligned with a longitudinal axis of shaft 120), and end effector 140 is maintained in an actuated state. Stated differently, actuators 110, 112 may be positioned along an intermediate portion of tracks 108, 109 such that wires 170, 172 are maintained at a neutral position relative to shaft 120 and end effector 140. In this instance, first wire 170 does not apply a tensile force onto second jaw 144B, and second wire 172 does not apply a tensile force onto first jaw 144A, thereby maintaining end effector 140 in the actuated state and distal articulation joint 130 in an unarticulated state (e.g., parallel to shaft 120 and/or handle 102).

Referring now to FIG. 1B, first actuator 110 may be translated along first track 108 in the first direction A (e.g., proximally) to pull first wire 170 proximally relative to shaft 120 and handle 102. In this instance, first actuator 110 may be moved to a proximalmost position, and configured to articulate distal articulation joint 130 toward a side of handle 102 including first actuator 110, thereby moving end effector 140 radially outward and in the first direction A. For example, a user of medical device 100 may move first actuator 110 relative to handle 102 by pulling first actuator 110 proximally toward proximal end 104. First actuator 110 may slide relative to handle 102 in response to applying a proximal force on grasping feature 114. In this instance, first wire 170 (secured to a body of first actuator 110 along a portion within handle 102) may move with grasping feature 114 in the first direction A relative to handle 102. With first wire 170 secured to proximal arm 144B, first actuator 110 may be configured to move first wire 170 relative to handle 102 and shaft 120.

First actuator 110 may pull first wire 170 proximally to apply a proximal (pulling) force onto proximal arm 148B, thereby causing distal articulation joint 130 to bend. In this instance, end effector 140 may be deflected in the first direction A, i.e. the same direction of movement as first actuator 110 relative to handle 102, since a connection point between wire 170 and arm 148B is off-center and radially outward of a longitudinal axis of distal articulation joint 130, towards a same side of medical device 100 as first actuator 110. A user of medical device 100 may selectively adjust a degree of articulation of distal articulation joint 130, and the corresponding extent of deflection of end effector 140, in response to a degree of movement of first actuator 110 relative to handle 102. Further, handle 102 may be rotated, to rotate shaft 120 and move end effector 140 relative to the target treatment site to facilitate further movement of medical device 100 toward a target object within the target treatment site. In some embodiments, second actuator 112 may remain stationary during translation of first actuator 110 relative to handle 102.

Still referring to FIG. 1B, second actuator 112 may be translated along second track 109 in the second direction B, that is opposite of the first direction A, to push second wire 172 distally relative to shaft 120 and handle 102. In this instance with distal articulation joint 130 already articulated by first actuator 110, second actuator 112 may be moved to a distalmost position, thereby causing end effector 140 to transition from an actuated state (FIG. 1A) to an unactuated state. For example, a user of medical device 100 may move second actuator 112 relative to handle 120 by sliding second actuator 112 distally toward distal end 106 to the distalmost position. Second actuator 112 may slide relative to handle 120 in response to applying a distal force on grasping feature 116. In this instance, second wire 172 (secured to a body of second actuator 112 along a portion within handle 102) may move with grasping feature 116 relative to handle 102. With second wire 170 secured to proximal arm 144A, second actuator 112 may be configured to move second wire 172 relative to handle 102 and shaft 120.

Second actuator 112 may push second wire 172 distally to apply a distal (pushing) force onto the proximal arm 144A, thereby causing first jaw 148A to move about pin 146 and away from second jaw 148B. In this instance, end effector 140 may be transitioned to the unactuated state with jaws 148A, 148B disengaged from one another. A user of medical device 100 may selectively adjust a degree of disengagement between jaws 148A, 148B in response to an extent of translation of second actuator 112 relative to second track 109. Stated differently, a gap formed between jaws 148A, 148B may correspond to a longitudinal translation of second actuator 112 along handle 102. In some embodiments, first actuator 110 may remain stationary during translation of second actuator 112 relative to handle 102.

End effector 140 may be maneuvered about the target treatment site by manipulating a position, orientation, and/or configuration of handle 102 with the grasping feature at proximal end 104 to position end effector 140 adjacent to the target object. With the target object positioned between an opening formed between jaws 148A, 148B, second actuator 112 may be translated proximally in the first direction A (e.g., to a neutral and/or proximalmost position) to move first jaw 148A toward second jaw 148B, and clamp the target object (e.g., tissue) therebetween.

It should be appreciated that actuators 110, 112 may provide multi-functional capabilities depending on a sequence of actuation of each actuator 110, 112 relative to one another. For example, in other embodiments, second actuator 112 may be moved in the first direction A (e.g., to the proximalmost position) in lieu of first actuator 110, such that distal articulation joint 130 may bend toward second actuator 112 and in the first direction A. In this instance, subsequent actuation of first actuator 110 in the second direction B (e.g., to the distalmost position) may provide movement of second jaw 148B relative to first jaw 148A to transition end effector from the closed configuration to the open configuration. With both actuators 110, 112 capable of articulating shaft 120 and actuating end effector 140, medical device 100 may provide an ergonomic interface for manipulating a target object (e.g., tissue) during a procedure with a single hand of a user. Further, medical device 100 may provide multiple degrees of articulation and/or directions of movement via actuators 110, 112.

Referring now to FIG. 7, another exemplary medical device 200 is depicted according to an example of the disclosure. Except as otherwise described herein, medical device 200 may be configured and operable similar to medical device 100. Accordingly, like reference numerals are used to identify like components.

Medical device 200 may include a handle 202 having a longitudinal length defined between a proximal end 204 and a distal end 206. Handle 102 may be sized, shaped, and configured to be graspable by a user of medical device 200. That is, handle 202 may provide an ergonomic interface for grasping medical device 200 and maneuvering handle 202 with a single hand. Handle 202 may further include a pair of tracks positioned along opposing sides of handle 202, and extending between proximal end 204 and distal end 206. For example, handle 202 may include a first track 208 along a top wall of handle 202 and a second track (not shown) positioned along a bottom wall of handle 202. Each track may define a travel path of one or more actuators 210, 212, and a longitudinal length of the tracks may define an articulation and actuation extent of medical device 200.

Medical device 200 may further include a pair of actuators 210, 212 movably coupled to handle 202 at the tracks. For example, medical device 200 may include a first actuator 210 slidably coupled to first track 208, and a second actuator 212 slidably coupled to the second track. In the example, first track 208 and the second track may include openings formed along an exterior of handle 202, such that actuators 210, 212 may be at least partially disposed within the openings and seated inside handle 202. First actuator 210 may be configured to translate along first track 208, and second actuator 212 may be configured to translate along the second track in one or more directions (e.g., proximally, distally, etc.). Although not shown, it should be understood that first actuator 210 may be coupled to first wire 170 within handle 202, and second actuator 212 may be coupled to second wire 172 within handle 202. Accordingly, each actuator 210, 212 may be configured to move the corresponding wire 170, 172 relative to handle 202 in response to translating along the respective track.

Still referring to FIG. 7, first actuator 210 may include a body with a grasping feature 214, and second actuator 212 may include a body with a grasping feature 216. Each grasping feature 214, 216 may be configured to facilitate movement of the respective actuator 210, 212 relative to the corresponding track. In the example, grasping features 214, 216 may include a slidable button and/or knob that is sized and shaped to receive a finger of a user thereon. It should be appreciated that grasping features 214, 216 may have various other suitable sizes, shapes, and/or configurations without departing from a scope of this disclosure.

Medical device 200 may further include shaft 120 extending distally from handle 202, and particularly from distal end 206. Although not shown, it should be understood that medical device 200 may include proximal shaft 122 and distal articulation joint 130, with end effector 140 coupled to a distal end of articulation joint 130. Medical device 200 may be configured and operable similar to medical device 100 described above, such that movement of actuators 210, 212 relative to handle 202 may provide a similar articulation and actuation of shaft 120 and end effector 140, respectively, as described in detail above with respect to medical device 100.

Each of the aforementioned systems, devices, assemblies, and methods may be used to manipulate target tissue with enhanced degree of maneuverability. By providing a medical device with an intuitive handle capable of controlling an actuation and articulation of an end effector with a single hand, a user may utilize another hand to control other devices and/or tools during a procedure for treating the target site. In this instance, a user may reduce overall procedure time, increase efficiency of procedures, and/or avoid unnecessary harm to a subject's body caused by limited control of the other tools/devices.

It will be apparent to those skilled in the art that various modifications and variations may be made in the disclosed devices and methods without departing from the scope of the disclosure. Other aspects of the disclosure will be apparent to those skilled in the art from consideration of the specification and practice of the features disclosed herein. It is intended that the specification and examples be considered as exemplary only.

We claim:

1. A medical device, comprising:
a handle;
a shaft extending distally from the handle;
an end effector extending distally from the shaft;
a first actuator movably coupled to the handle; and
a second actuator movably coupled to the handle;
wherein the first actuator is configured to (1) articulate the shaft in response to translating the first actuator in a first direction relative to the handle and the second actuator, and (2) actuate the end effector in response to translating the first actuator in a second direction relative to the handle and the second actuator; and
wherein the second actuator is configured to (1) articulate the shaft in response to translating the second actuator in the first direction relative to the handle and the first actuator, and (2) actuate the end effector in response to translating the second actuator in the second direction relative to the handle and the first actuator.

2. The medical device of claim 1, wherein the handle includes a first track extending along a body of the handle; and
wherein the first actuator is received within the first track and configured to translate along the first track.

3. The medical device of claim 2, wherein the first track has a longitudinal length that corresponds to (1) a first degree of articulation of the shaft; and (2) a first extent of actuation of the end effector.

4. The medical device of claim 3, wherein the handle includes a second track extending along the body of the handle; and
wherein the second actuator is received within the second track and configured to translate along the second track.

5. The medical device of claim 4, wherein the second track has a longitudinal length that corresponds to (1) a second degree of articulation of the shaft; and (2) a second extent of actuation of the end effector.

6. The medical device of claim 1, further including a first wire and a second wire disposed within the handle and the shaft;
wherein the first wire is coupled to the first actuator and a first part of the end effector; and
wherein the second wire is coupled the second actuator and a second part of the end effector.

7. The medical device of claim 6, wherein the first actuator is configured to move the first wire in the first direction to articulate the shaft and move the first part and the second part in the first direction; and
wherein the second actuator is configured to move the second wire in the second direction to move the second part relative to the first part.

8. The medical device of claim 7, wherein the second actuator is configured to move the second wire in the first direction to articulate the shaft and move the first part and the second part in the first direction; and
wherein the first actuator is configured to move the first wire in the second direction to move the second part relative to the first part.

9. The medical device of claim 6, wherein the first actuator is configured to move the first part relative to the second part, and the second actuator is configured to move the second part relative to the first part.

10. The medical device of claim 1, wherein the first actuator is configured to articulate the shaft toward the first actuator and in the first direction in response to translating the first actuator in the first direction relative to the handle and the second actuator.

11. The medical device of claim 10, wherein the second actuator is configured to articulate the shaft toward the second actuator and in the first direction in response to translating the second actuator in the first direction relative to the handle and the first actuator.

12. The medical device of claim 1, wherein the first actuator and the second actuator are disposed about a circumference of the handle.

13. The medical device of claim 1, wherein the first actuator and the second actuator are at least partially disposed within the handle.

14. The medical device of claim 1, wherein the first actuator includes a first finger ring, the second actuator includes a second finger ring, and the handle includes a third finger ring; and
　　wherein the third finger ring is fixed relative to the first and the second finger rings, and the first and the second finger rings are movable relative to one another and the third finger ring.

15. The medical device of claim 1, wherein the first actuator has a proximalmost position corresponding to an articulated position of the shaft, a distalmost position corresponding to an actuated position of the end effector, and a neutral position between the proximalmost position and the distalmost position, and corresponding to an unarticulated position of the shaft and an unactuated position of the end effector.

16. A medical device, comprising:
　　a handle having a first movable actuator and a second movable actuator;
　　a shaft extending distally from the handle and having an end effector at a distal end of the shaft;
　　a first wire disposed within the shaft and coupled to the first movable actuator and the end effector; and
　　a second wire disposed within the shaft and coupled to the second movable actuator and the end effector;
　　wherein the first movable actuator is configured to (1) articulate the shaft in response to translating the first wire proximally relative to the shaft and the second movable actuator, and (2) actuate the end effector in response to translating the first wire distally relative to the shaft and the second movable actuator; and
　　wherein the second movable actuator is configured to (1) articulate the shaft in response to translating the second wire proximally relative to the shaft and the first movable actuator, and (2) actuate the end effector in response to translating the second wire distally relative to the shaft and the first movable actuator.

17. The medical device of claim 16, wherein the handle includes a first track and a second track extending along opposing sides of the handle; and
　　wherein the first movable actuator is received within the first track and configured to translate along the first track, and the second movable actuator is received within the second track and configured to translate along the second track.

18. The medical device of claim 17, wherein the first track has a first longitudinal length that corresponds to (1) a first degree of articulation of the shaft; and (2) a first extent of actuation of the end effector; and
　　wherein the second track has a second longitudinal length that corresponds to (1) a second degree of articulation of the shaft; and (2) a second extent of actuation of the end effector.

19. The medical device of claim 16, wherein the first movable actuator is configured to articulate the shaft toward the first movable actuator and in a first direction in response to translating the first movable actuator in the first direction relative to the handle and the second movable actuator; and
　　wherein the second movable actuator is configured to articulate the shaft toward the second movable actuator and in the first direction in response to translating the second movable actuator in the first direction relative to the handle and the first movable actuator.

\* \* \* \* \*